United States Patent [19]

Schlegel et al.

[11] Patent Number: 4,835,180

[45] Date of Patent: May 30, 1989

[54] N-(ω-CYANOALKYL)AMINOPHENOLS AND USE AS INHIBITORS OF LIPOXYGENASE ACTIVITY

[75] Inventors: Donald C. Schlegel, Schodack; Robert E. Johnson, East Greenbush, both of N.Y.

[73] Assignee: Sterling Drug Inc., New York, N.Y.

[21] Appl. No.: 914,424

[22] Filed: Oct. 2, 1986

[51] Int. Cl.$^4$ .................. A61K 31/275; C07C 121/52
[52] U.S. Cl. ...................................... 514/523; 558/394
[58] Field of Search ................. 558/394; 514/523, 527

[56] References Cited

U.S. PATENT DOCUMENTS

| | | | |
|---|---|---|---|
| 2,809,983 | 10/1957 | Heininger | 558/394 |
| 3,231,601 | 1/1966 | Peterli | 558/394 |
| 3,496,213 | 2/1970 | Ross | 558/394 |
| 3,743,668 | 7/1973 | Scully | 558/394 |
| 4,386,031 | 5/1983 | Hilboll et al. | 260/704 |

FOREIGN PATENT DOCUMENTS 1326824 8/1973 United Kingdom .

OTHER PUBLICATIONS

Wagner et al., "Synthetic Organic Chemistry", (1953), pp. 566, 660 591, and 481.
McOmie, "Protective Groups in Organic Chemistry", (1973), pp. 44, 88–89 and 101.
Greene "Protective Groups in Organic Synthesis", (1982), pp. 145, 146, and 218 to 222.
S. A. Heininger *J. Org. Chem.* 22, 1213–1217 (1957).
D'Amico et al., *J. Am. Chem. Soc.* 81, 5957–5963 (1959).
Aliev et al., C. A. 96: 217407e.
Peshakova et al., C. A. 96: 52211w.
D. A. Simov et al. *Doklady Bolganskoj Akademija Nauk* 32, 1365–1368 (1979).
Mukhamedov et al. (CA 99: 5304f).
Nitzschke and Budka *Chem. Ber.* 88, 264 (1955).

*Primary Examiner*—Anton H. Sutto
*Attorney, Agent, or Firm*—Philip E. Hansen; Paul E. Dupont

[57] ABSTRACT

N-(ω-cyanoalkyl)aminophenols of formula

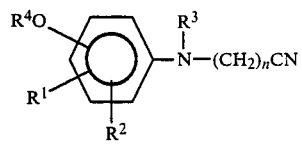

useful as lipoxygenase inhibitors and anti-asthmatic agents, are prepared by acylation of an aminophenol with an ω-haloalkanoyl chloride followed by reduction of the resulting amide then displacement of the halide by cyanide.

32 Claims, No Drawings

N-(ω-CYANOALKYL)AMINOPHENOLS AND USE AS INHIBITORS OF LIPOXYGENASE ACTIVITY

BACKGROUND OF THE INVENTION (1) Field of the Invention

The present invention relates to novel N-(ω-cyanoalkyl)aminophenols, a process for the preparation thereof, and the use of said aminophenols as agents which inhibit lipoxygenase activity.

(2) Information Disclosure Statement

S. A. Heininger U.S. Pat. No. 2,809,983 issued Oct. 15, 1957 discloses 3-(p-hydroxyanilino)propionitrile, 3-(o-hydroxyanilino)propionitrile, and 3-(m-hydroxyanilino)propionitrile as agricultural antifungals, rubber additives, chemical intermediates and biological toxicants. S. A. Heininger *J. Org. Chem.* 22, 1213–1217 (1957) makes substantially the same disclosure.

D'Amico et al., *J. Am. Chem. Soc.* 81, 5957–5963 (1959) discloses without utility at page 5961 3-(2-hydroxy-5-nitrosoanilino)propionitrile.

D. F. Scully U.S. Pat. No. 3,743,668 issued July 3, 1973, discloses 3-(p-hydroxyanilino)propionitrile, 3-(o-hydroxyanilino)propionitrile, and 3-(m-hydroxyanilino)propionitrile and a process for their preparation.

Aliev et al. *Uzb. Khim. Ch.* 1981, 45–49 (C.A. 96: 217407e) discloses 3-(o-hydroxyanilino)propionitrile. Similarly Peshakova et al. *Khim. Geterotsikl. Soedin.* 1981, 1420 (C.A. 96: 52211w) and D. A. Simov et al. *Doklady Bolganskoj Akademija Nauk* 32, 1365–1368 (1979) disclose only as starting material 3-(o-hydroxyanilino)propionitrile.

H. J. Peterli U.S. Pat. No. 3,213,601 issued Jan. 25, 1966 discloses 3-(p-hydroxyanilino)propionitrile, 3-(o-hydroxyanilino)propionitrile, and 3-(m-hydroxyanilino)propionitrile and a process for their production. J. M. Ross U.S. Pat. No. 3,496,213 issued Feb. 17, 1970 discloses the same three hydroxyanilinopropionitriles and a different process for their production.

British Pat. No. 1,326,824 published Aug. 15, 1973, which is equivalent to Ger. Offen. 2,000,509, discloses as a coupling component for azo dyes 3-(2-hydroxy-5-nitroanilino)propionitrile and a process for its production.

Mukhamedov et al. *Uzb. Khm. Zh.* 1983, 53 (CA 99: 5304f) discloses without utility 3-[(5-chloro-2-hydroxyphenyl)amino]propanenitrile.

Nitzschke and Budka *Chem. Ber.* 88, 264 (1955) discloses without utility 7-anilinoheptanenitrile.

Hilboll et al. U.S. Pat. No. 4,386,031 issued May 31, 1983 discloses N-benzoyl-ω-anilinoalkanecarboxylic acids and their derivatives of the general formula

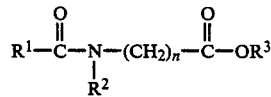

wherein n is a positive integer ranging from 7 to 10, $R^1$ and $R^2$, which may be identical or different from each other, represent the unsubstituted phenyl group or the phenyl groups substituted by one to four equal or different radicals selected from the group of halogen, in particular chlorine or fluorine; $C_{1-4}$ alkyl, in particular methyl; $C_{1-4}$ alkoxy, in particular methoxy or ethoxy; $C_{1-4}$ alkylthio, in particular methylmercapto or ethylmercapto; acyloxy, in particular $C_{1-4}$ alkanacyl, most preferably acetoxy, propionyloxy or benzoyloxy; halo $C_{1-4}$ alkyl, in particular trifluoromethyl; hydroxy; phenoxy; benzyloxy; di-$C_{1-4}$ alkylamino, in particular dimethylamino; $R^3$ is hydrogen, an alkali metal ion, in particular the sodium metal ion or a straight or branched saturated hydrocarbon group having from one to seven carbon atoms such as and in particular ethyl, isopropyl or heptyl; or the benzyl group. In most pertinent part U.S. Pat. No. 4,386,031 discloses at columns 14–16 (Example 13) 8-[4-chloro-N-(4-hydroxyphenyl)-benzamido]caprylic acid. The patent discloses that the benzoyl anilinoalkane carboxylic acids and their derivatives possess antiallergic activity and are useful for the treatment of allergic and asthmatic diseases.

SUMMARY OF THE INVENTION

In a product aspect, the invention relates to compounds of the formula

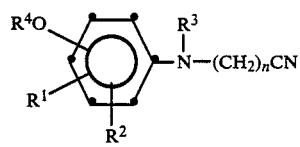

or acid addition salts thereof wherein $R^1$ and $R^2$ may be the same or different and are chosen from the group consisting of hydrogen, lower-alkyl, lower-alkoxy, lower-alkylthio, hydroxy lower-alkyl, and halo;

$R^3$ is hydrogen or lower-alkyl;

$R^4O$ is 2- or 4-hydroxy or 2- or 4-lower-acyloxy;

n is an integer from four to twelve.

Lower-alkyl and lower-acyl herein describe substituents consisting of four or fewer carbons in branched or straight chains.

In a further product aspect, the invention relates to compositions for inhibiting lipoxygenase activity which comprise a compound of formula I or acid addition salt thereof together with one or more pharmaceutically acceptable excipients or diluents.

In a process aspect, the invention relates to a process for preparing a compound of formula I which comprises acylation of an aminophenol of formula II,

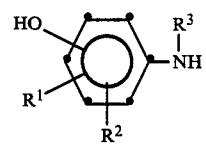

wherein $R^1$, $R^2$, and $R^3$ are as defined above, with an activated ω-halo acid of formula III wherein n is as defined above, X is a halogen and Y is an acyl-activating group such as halogen, substituted phenoxy, imidoxy or acyloxy; followed by reduction of the resulting amide and displacement of halide by cyanide. When it is desired that $R^4$ be lower acyl, the phenol may be acylated by a suitably activated acid.

In a further process aspect the invention relates to a process for preparing a compound of formula I which comprises diprotection of an aminophenol; base-catalyzed alkylation of the protected nitrogen with an ω-haloalkylnitrile, X—$(CH_2)_n$CN, wherein X and n are as defined above; and deprotection.

In a still further process aspect, the invention relates to a method for inhibiting lipoxygenase activity, including prevention or treatment of allergic asthma, in a mammal which comprises administering to said mammal a pharmacologically effective amount of a composition comprising a compound of formula I or pharmaceutically acceptable acid addition salt thereof together with one or more pharmaceutically acceptable excipients or diluents.

DETAILED DESCRIPTION INCLUSIVE OF PREFERRED EMBODIMENTS

In the following formulas I–V the variables $R^1$, $R^2$, $R^3$, X, Y and n are as defined hereinabove. $R^{4*}$ is lower acyl.

The preferred synthesis of compounds of the invention may be outlined as follows:

afford N-(ω-cyanoalkyl)aminophenol Ia (formula I where $R_4$ is hydrogen). The reaction may be run at about 25° to 100° C., preferably at 80° to 95° C. In the case where n is 4 or 5 it may be desirable to mask the basicity of the aniline nitrogen with a removable protecting group before displacing with cyanide to preclude the formation of N-aryl pyrrolidines or N-aryl piperidines. The protecting group chosen must of course be removable under conditions which are compatible with the integrity of the functionalities of compounds of formula I. Examples of such protecting groups are trifluoroacetamides or t-butyl urethanes.

An optional fourth step consists of reacting the free phenol, Ia where $R^3$ is lower alkyl, with an activated lower-alkyl acid $R^{4*}Y$ wherein $R^{4*}$ is lower-acyl, to produce the ester Ib (formula I where $R^3$ is lower alkyl and $R_4$ is lower-acyl). The reaction is run at about 0° to 50° C. in an inert organic solvent, or, in the case where $R^{4*}Y$ is an anhydride, the anhydride may be used as the solvent and an alkali metal salt of $R^{4*}OH$ may be used as a base.

A second synthesis of compounds of the invention may be outlined as follows:

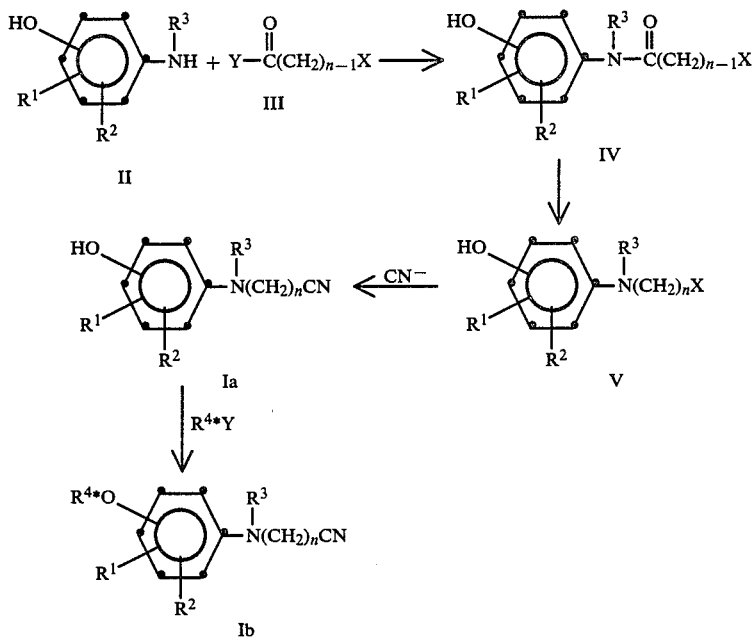

A suitably substituted aminophenol (II) is caused to react with a suitably activated ω-halo acid (III), preferably an ω-bromoacyl chloride, to give the amide IV. The reaction is carried out in an appropriate organic solvent, such as acetone, from about −5° C. to the boiling point of the solvent. An external base such as N,N-dimethylaniline may be employed as an acid acceptor, or a second mole of aminophenol may function as the base.

The amide (IV) is reduced, preferably with diborane or more preferably with borane-methyl sulfide, to produce an ω-haloalkylaniline of formula V. The reduction is carried out in an inert organic solvent, such as THF, between about 0° C. and the reflux temperature of the solvent.

In the third step the halogen, of the ω-haloalkylaniline (V), is replaced by a nitrile function, preferably by displacement in a suitable solvent preferably DMSO, DMF or acetonitrile, most preferably DMSO, using a salt of hydrocyanic acid, preferably sodium cyanide, to

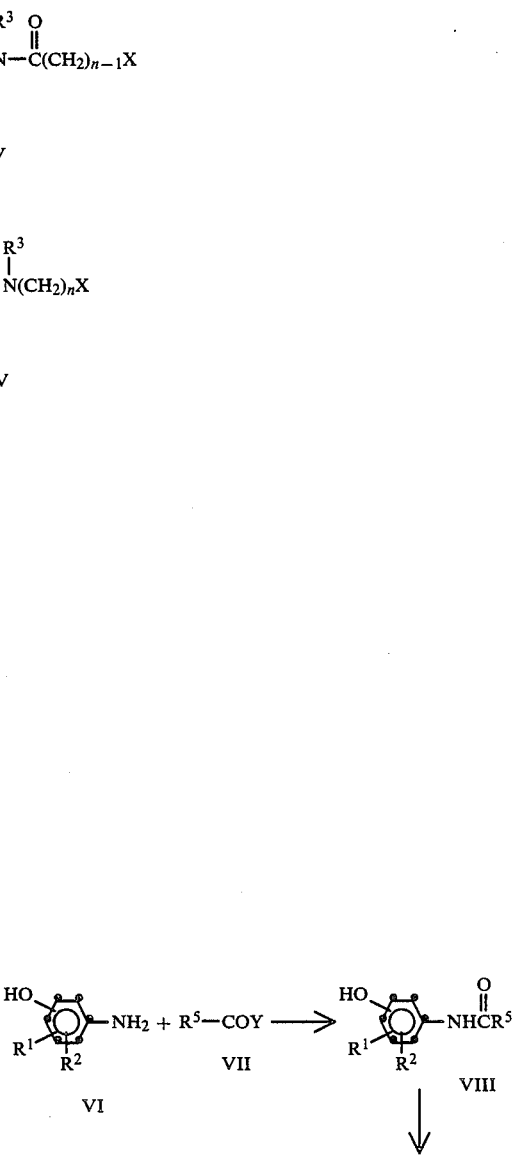

-continued

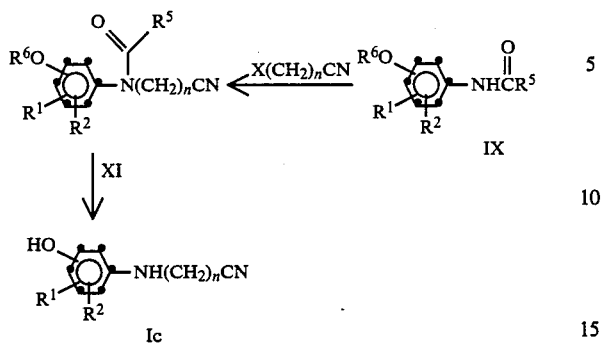

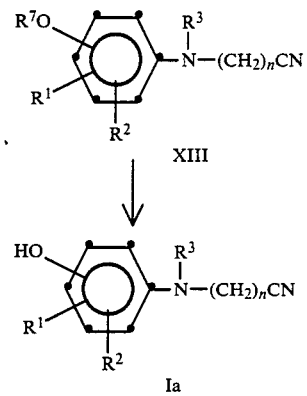

A suitably substituted aminophenol (VI) is caused to react with an activated acid (VII) wherein $R^5$ is t-butyloxy or, preferably, trifluoromethyl. The reaction is run in an appropriate organic solvent at about 0° to 40° C. The resulting phenol-amide (VIII) is protected, preferably as its tetrahydropyranyl ether, and the protected phenol-amide (IX, wherein $R^6$ is t-butyl, tetrahydropyranyl or other acid-labile ether-forming residue) is alkylated with an ω-haloalkyanenitrile (X), preferably ω-bromoalkanenitrile, under basic conditions using an alkali metal hydride or fluoride such as sodium or potassium hydride or cesium fluoride or an alkali metal hydroxide, bicarbonate, or carbonate, most preferably potassium carbonate at about 25° to 110° C. in a suitable solvent such as DMF to give the cyanoalkylamide (XI). In the fourth step the protecting group is cleaved by mild acid to give the N-(ω-cyanoalkyl)aminophenol Ic (formula I where $R^3$ and $R^4$ are hydrogen).

A third synthesis of compounds of the invention consists of reacting an oxygen-protected aniline (XII) wherein $R^7$ is lower alkyl, preferably t-butyl, or aralkyl, most preferably benzyl, with an ω-haloalkanenitrile (X), preferably an ω-bromoalkanenitrile, in the presence of an alkali metal base, preferably CsF, using the solvents and conditions described above, to give the cyanoalkylaniline (XIII) followed by deprotection of the oxygen with an appropriate mineral acid such as HBr at about 0° to 50° C. to produce N(ω-cyanoalkyl)aminophenol Ia. The synthesis may be outlined as follows:

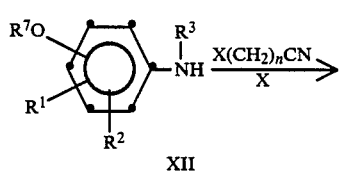

A synthesis of compounds of the invention wherein $R^3$ is hydrogen and $R^4$ is lower-acyl, formula Id, consists of reacting a suitably substituted aminophenol of formula Ic (I where $R^3$ and $R^4$ are H) with an appropriate activated acyl compound of formula $R^5COY$, preferably di-t-butyldicarbonate at about 0° to 50° C. in a suitable solvent to produce preferably a t-butylurethane of formula XIV, ($R^5$=OC(CH$_3$)$_3$). The phenol-urethane XIV is reacted with the appropriately activated lower-alkyl acid $R^{4*}Y$, preferably the anhydride of the lower-alkyl acid, at 0° to 50° C. in an inert, organic solvent, or, in the case where $R^{4*}Y$ is an anhydride, the anhydride may be used as the solvent and an alkali metal salt of $R^{4*}OH$ may be used as a base. The acyl protecting group $R^5CO$ is cleaved by anhydrous mineral acid or trifluoroacetic acid optionally in the presence of a suitable organic solvent at about 0° to 50° C.:

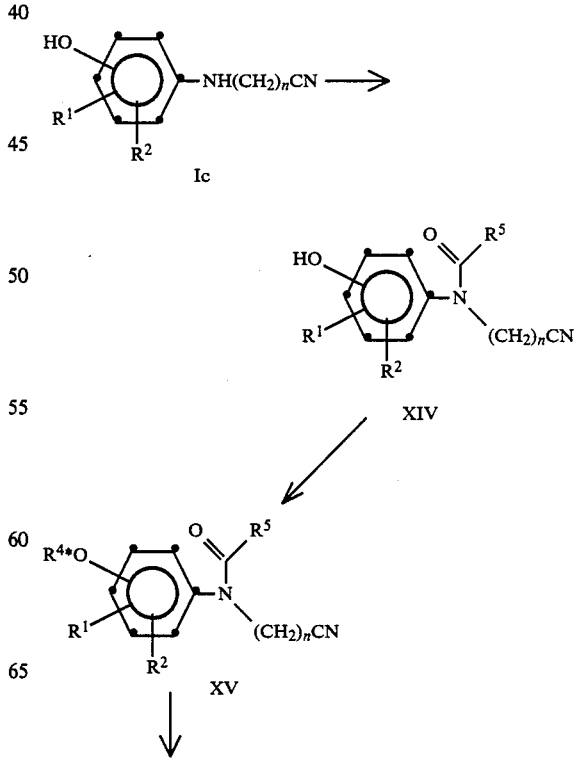

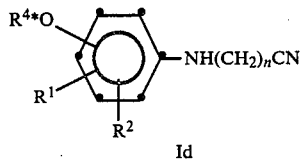

Id

The compounds of formula I are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts that is, salts whose anions are relatively innocuous to the animal organism in medicinal doses of the salts so that the beneficial properties inherent in the free base are not vitiated by side effects ascribable to the anions. In practicing our invention we found it convenient to form the hydrochloride or maleate salts. However, other appropriate medicinally acceptable salts within the scope of the invention are those derived from mineral acids and organic acids. The acid-addition salts of the basic compounds are prepared either by dissolving the free base in aqueous alcohol solution containing the appropriate acid and isolating the salt by evaporating the solution, or by reacting the free base and an acid in organic solvent, in which case the salt separates directly, is precipitated with a second organic solvent, or can be obtained by concentration of the solution. Although medicinally acceptable salts of the basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared and nuclear magnetic resonance spectroscopy. The course of the reactions and the identity and homogeneity of the products were assessed by thin layer chromatography. The starting materials are either commercially available or may be prepared by procedures well known in the art.

The following examples will further illustrate the invention.

EXAMPLE 1

(a) 4-Bromo-N-(4-hydroxyphenyl)butanamide [IV; $R^1=R^2=R^3=H$ X=Br, n=4]

A mixture of 30.9 g (0.28 mol) of p-aminophenol in about 300 mL of acetone was stirred in an ice bath and a solution of 25 g (0.14 mol) of 4-bromobutyryl chloride in about 50 mL of acetone was dripped in over 20 minutes. The reaction was stirred cold for another ½ hour and then at room temperature for two hours. It was then ice cooled and the mixture filtered. The precipitate was washed with about 200 mL of cold acetone. The filtrate was evaporated and the residue slurried in about 200 mL of 1N HCl, whereupon a precipitate formed. The mixture was ice cooled, filtered, and the precipitate was washed with additional 1N HCl followed by water. The precipitate was dissolved in about 100 mL of ethanol at room temperature, diluted with about 160 mL of water, ice cooled and filtered. The precipitate was washed with a mixture of water and ethanol and then with hexane to yield 18.1 g (52%) of 4-bromo-N-(4-hydroxyphenyl)butanamide, mp 142.5°–144.5° C.

(b) 4-[(4-Bromobutyl)amino]phenol [V; $R^1=R^2=R^3=H$, X=Br n=4]

A solution of 18.06 g (0.07 mol) of 4-bromo-N-(4-hydroxyphenyl)butanamide in about 120 mL of THF was filtered to remove 0.6 g of a solid and placed in a 2 L flask under nitrogen. It was stirred magnetically in an ice bath while 280 mL (0.28 mol) of 1M borane-THF complex was dripped in over 20 minutes. The reaction was stirred cold for ½ hour, then at room temperature for 15 minutes, then at reflux for two hours on a steam bath. The reaction was cooled with an ice bath and diluted with 275 mL of methanol followed by 20 mL of 8N ethanolic HCl. This solution was heated at reflux for six hours on a steam bath and then allowed to stand at room temperature overnight. The next morning the solution was evaporated and the residue was dissolved in acetonitrile and evaporated again. The oily residue was slurried three times with ether and the ether decanted after each addition. After the last decanting the solution was evaporated on a rotary evaporator to yield an oil which was taken to the next step without further purification.

(c) 5-[(4-Hydroxyphenyl)amino]pentanenitrile [I; $R^1=R^2=R^3=R^4=H$, n=4]

The oily 4-[(4-bromobutyl)amino]phenol from part b and 20 mL of trifluoroacetic anhydride were stirred together on an ice bath and then at room temperature. After two hours another 10 mL of trifluoroacetic anhydride was added, and after a further hour another 10 mL of trifluoroacetic anhydride was added, and the reaction was warmed on a warm water bath for one hour. It was then poured into 250 mL of ice and water and extracted three times with ethyl acetate. The ethyl acetate extracts were washed with a mixture of water and saturated sodium chloride solution and dried over magnesium sulfate. The solution was evaporated, the residue diluted with toluene and evaporated again to give 29.7 g of slightly impure, oily N-(4-bromobutyl)-N-(4-hydroxyphenyl)trifluoroacetamide, containing some toluene.

Sodium cyanide (17.2 g, 0.35 mol) was stirred mechanically in 325 mL DMSO under nitrogen and heated to 64° C. The 29.7 g of N-(4-bromobutyl)-N-(4-hydroxyphenyl)trifluoroacetamide in 125 mL of DMSO was dripped in over 1¾ hours. The reaction was stirred for two hours at 65°–72° C., cooled to −15° C., and poured into 3 L of ice and water. The cold mixture was immediately acidified with about 350 mL of 1N HCl and extracted three times with a total of 1.2 L of ethyl acetate. The ethyl acetate extracts were washed once with saturated sodium chloride solution and dried over magnesium sulfate. The solution was evaporated on a rotary evaporator to yield 11.5 g of N-(4-cyanobutyl)-N-(4-hydroxyphenyl)trifluoroacetamide.

To a solution of 30 g of potassium carbonate dissolved in 90 mL of water and 210 mL of methanol under nitrogen was added the 11.5 g of N-(4-cyanobutyl)-N-(4-hydroxyphenyl)trifluoroacetamide and the reaction was heated at 48°–53° C. for 4½ hours. The reaction was allowed to stand at room temperature 18 hours and then acidified with 18 mL of acetic acid. Most of the methanol was evaporated and the remaining solution was diluted with a little water and ethyl acetate and made basic with solid potassium bicarbonate. The layers were separated and the aqueous phase was reextracted with ethyl acetate. The ethyl acetate extracts were washed with saturated NaCl solution and dried over anhydrous sodium sulfate. Evaporation of the ethyl acetate solution and trituration in hexane gave a solid which was dissolved in 15 ml of acetone and filtered through a short column of silica gel using acetone-hexane (40:60). The solvent was evaporated and the resulting solid was sublimed at 0.07 mm/125° C. then recrystallized from THF-hexane to yield 2.95 g of 5-[(4-hydroxyphenyl)amino]pentanenitrile, mp 88°–90° C., (22% yield from 4-bromo-N-(4-hydroxyphenyl)butanamide).

EXAMPLE 2

(a) 6-Bromo-N-(4-hydroxyphenyl)hexanamide [IV; $R^1=R^2=R^3=H$, X=Br, n=6]

was prepared in 88% yield from 148.4 g (1.36 mol) of p-aminophenol and 145 g (0.68 mol) of 6-bromohexanoyl chloride according to the procedure of Example 1, part a, except that the addition was made at ambient temperature and the reaction was refluxed one hour, mp 124°–125° C.

(b) 4-[(6-Bromohexyl)amino]phenol [V; $R^1=R^2=R^3=H$, X=Br, n=6]

was prepared from 35 g (0.12 mol) of 6-bromo-N-(4-hydroxyphenyl)hexanamide according to the procedure of Example 1, part b. The product, which was obtained in 91% yield, was crystallized from acetonitrile to mp 123°–126° C. and contained approximately 16% of 4-[(6-chlorohexyl)amino]phenol. It was used in this form in the reaction of part d.

(c) Alternatively, the reduction was carried out utilzing borane-methylsulfide complex in place of borane-THF complex as follows. A solution of 42.3 g (0.15 mol) of 6-bromo-N-(4-hydroxyphenyl)hexanamide in 250 mL of THF was cooled to 5° C. and 54 mL (0.54 mol) of 10M boroanemethylsulfide was added dropwise over seven minutes. After addition, the reaction was heated on a steam bath for three hours, cooled on ice, and 250 mL of methanol was added. The reaction was stirred briefly and 23 mL of 48% HBr was added. The reaction was refluxed for two hours and then concentrated in vacuo to an oil which was crystallized from 200 mL of acetonitrile. A second crop was obtained by adding 25 mL of 48% HBr to the acetonitrile mother liquor. The combined yield was 50.0 g (96%) of 4-[(6-bromohexyl)amino]phenol hydrobromide, mp 98°–102° C.

(d) 7-[(4-Hydroxyphenyl)amino]heptanenitrile [I; $R^1=R^2=R^3=R^4=H$, n=6]

A solution of 58.6 g (0.19 mol) of 4-[(6-bromohexyl)amino]phenol from part b in about 400 mL of DMF was added dropwise to a slurry of 46.6 g (0.95 mol) of sodium cyanide in 370 mL of DMF in a 2 L flask at 70° C. over the course of two hours. Heating was continued for two hours. After cooling, the reaction was filtered and diluted with about 2 L of water and extracted twice with ethyl acetate. The ethyl acetate extracts were combined, washed three times with saturated sodium chloride solution, and dried over magnesium sulfate. The solution was stripped to a red-orange solid which was dissolved in warm ethyl acetate, treated with decolorizing carbon, cooled, and recrystallized by the addition of a small amount of hexane to yield 7-[(4-hydroxyphenyl)amino]heptanenitrile, mp 75°–76° C., in 53% yield.

The hydrochloride salt was prepared from a solution of 7-[(4-hydroxyphenyl)amino]heptanenitrile in acetonitrile treated with ethanolic HCl, mp 136°–139° C.

In a subsequent run, utilizing the preferred conditions, 10 g (0.03 mol) of 4-[(6-bromohexyl)amino]phenol in 30 mL of DMSO was added to a slurry of 8 g (0.16 mol) of sodium cyanide in 20 mL DMSO stirred 95° C. over the course of 25 minutes. The reaction was stirred at 95° C. for 40 minutes and poured into 300 mL of ice water. The product was filtered off and dried to provide an 80% yield of free base.

Alternatively, 7-[(4-hydroxyphenyl)amino]heptanenitrile of Example 2d was prepared by the following route.

To a solution of 109 g (1 mol) of p-aminophenol and 92.9 mL (1.15 mol) of pyridine in 1 L of t-butylmethylether at −10° was added 156 mL (1.1 mol) of trifluoroacetic anhydride. During addition the temperature was maintained below 0° C. After the addition was complete, the temperature was allowed to rise to 15° C., at which point a saturated solution of sodium chloride was added and the reaction stirred rapidly for 15 minutes. The layers were separated and the organic layer washed twice with saturated sodium chloride solution, dried over magnesium sulfate, and concentrated in vacuo to yield 194.1 g (95%) of N-(4-hydroxyphenyl)-trifluoroacetamide. The 194 g (0.95 mol) of N-(4-hydroxyphenyl)trifluoroacetamide was slurried in 3 L of methylene chloride containing 500 mg of p-toluenesulfonic acid. The mixture was stirred at room temperature and 250 mL (2.73 mol) of dihydropyran was added dropwise over 30 minutes. The reaction was stirred 18 hours at room temperature and approximately 1 L of saturated sodium bicarbonate solution was added with vigorous stirring for 30 minutes. The methylene chloride layer was separated, dried over magnesium sulfate, and concentrated to yield a reddish solid which was recrystallized from about 400 mL of toluene to yield 239 g (87%) of N-[4-[(tetrahydropyran-2-yl)oxy]phenyl]trifluoroacetamide. The diprotected aminophenol (8.67 g, 0.03 mol) was dissolved in 60 mL of dry DMF and stirred vigorously with 12.4 g (0.09 mol) of milled potassium carbonate and 6.3 mL (0.075 mol) of 7-bromoheptanenitrile. The reaction was heated on a steam bath for 2¼ hours, then cooled, and a mixture of 50 mL of water, 30 mL of methanol and 15 g of potassium carbonate was added with stirring. The mixture was heated on a steam bath for one hour and then let stand 18 hours. The reaction was poured into water and extracted two times with ether. The ether layers were combined and washed with saturated sodium chloride solution three times, dried over magnesium sulfate, and concentrated in vacuo to yield 9.5 g (90%) of tetrahydropyranyl-protected 7-[(4-hydroxyphenyl)amino]heptanenitrile, containing less than 10% of 6-heptenenitrile. The alkylation was performed less satisfactorily using sodium hydride or cesium fluoride in place of milled potassium carbonate as the base, in which case a separate step using potassium carbonate in methanol-water was required to remove the trifluoroacetyl protecting group. The tetrahydropyranyl-protected product was stirred for one hour in 100 mL of 1.5N HCl. The reaction was washed with ether and the aqueous layer was slowly added to ice-cold, saturated sodium bicarbonate. The precipitate was washed with water and dried to yield 6.1 g of 7-[(4-hydroxyphenyl)amino]heptanenitrile.

Alternatively 7-[(4-hydroxyphenyl)amino]heptanenitrile of Example 2d was made by the following procedure.

A 20 g portion of 4-benzyloxyaniline hydrochloride was dissolved in chloroform-methanol and made basic with a solution of 70 mL of 1.25N sodium hydroxide and 70 mL of water. The layers were separated, the aqueous phase extracted with chloroform, the chloroform extracts washed with saturated sodium chloride solution, and dried over anhydrous sodium sulfate. The solvent was evaporated to yield 17 g of 4-benzyloxyaniline. A solution of 2 g (0.01 mol) of 4-benzyloxyaniline, 2.26 ml (0.015 mol) of 7-bromoheptanenitrile and 7.6 g (0.05 mol) of cesium fluoride in 20 mL of DMF was stirred and heated at 100° C. for two hours. The reaction was cooled and poured into saturated sodium chloride solution and extracted with ether. The ether extracts were washed three times with saturated sodium chloride solution, dried over magnesium sulfate and concentrated to 2.9 g of oil. The oil was chromatographed on 100 g of silica gel using a gradient from 10–30% ethyl acetate in hexane. There was obtained 2.55 g (85%) of 7-[(4-benzyloxyphenyl)amino]heptanenitrile. The benzyloxy compound was treated with eight parts of 48% HBr at room temperature for 5 hours to yield impure 7-[(4-hydroxyphenyl)amino]heptanenitrile.

EXAMPLE 3

(a) 6-Bromo-N-(2-hydroxyphenyl)hexanamide [IV; $R^1=R^2=R^3=H$, $X=Br$, $N=6$]

was prepared in 73% yield from 34.7 g (0.23 mol) of 2-aminophenol and 32 g (0.15 mol) of 6-bromohexanoyl chloride according to the procedure of Example 1, part a, except that the addition was made at room temperature and the crude product was dissolved in ethyl acetate and washed with 1N HCl. The 6-bromo-N-(2-hydroxyphenyl)hexanamide was recrystallized from ethyl acetate-hexane, mp 88°–90° C.

(b) 2-[(6-Bromohexyl)amino]phenol [V; $R^1=R^2=R^3=H$, $X=Br$, $n=6$]

was prepared in 81% yield from 30.6 g (0.11 mol) of 6-bromo-N-(2-hydroxyphenyl)hexanamide according to the procedure of Example 1, part b, except that the amide was added to the diborane (inverse addition). The product was crystallized from acetonitrile by the addition of chloroform and then ether, mp 124°–126° C.

(c) 7-[(2-Hydroxyphenyl)amino]heptanenitrile monohydrochloride[I; $R^1=R^2=R^3=R^4=H$, $n=6$]

was prepared in 79% yield from 31.6 g (0.10 mol) of 2-[(6-bromohexyl)amino]phenol and 26.5 g (0.51 mol) sodium cyanide by the first procedure of Example 2, part d, except that DMSO was used in place of DMF as the solvent. The 7-[(2-hydroxyphenyl)amino]heptanenitrile monohydrochloride was recrystallized from acetonitrile, mp 108°–109° C.

EXAMPLE 4

(a) 7-Bromo-N-(4-hydroxyphenyl)heptanamide [IV; $R^1=R^2=R^3=H$, $X=Br$, $n=7$]

was prepared in 98% yield from 25.9 g (0.23 mol) of 4-aminophenol and 25.3 g (0.11 mol) of 7-bromoheptanoyl chloride according to the procedure of Example 1, part a, except that the addition was made at room temperature. The 7-bromoheptanoyl chloride was obtained from the reaction of one equivalent of 7-bromoheptanoic acid with two equivalents of thionyl chloride for two hours at 90° C. in toluene and was distilled at 0.05 mm with a boiling point of 59°–60° C. The 7-bromo-N-(4-hydroxyphenyl)heptaneamide was recrystallized from ethanol-water, mp 104°–105° C.

(b) 4-[(7-Bromoheptyl)amino]phenol [V; $R^1=R^2=R^3=H$, $X=Br$, $n=7$]

was prepared in 95% yield from 32.6 g (0.11 mol) of 7-bromo-N-(4-hydroxyphenyl)heptanamide according to the procedure of Example 3, part b. The product was recrystallized from acetonitrile by the addition of ether, mp 121°–123° C.

(c) 8-[(4-Hydroxyphenyl)amino]octanenitrile (Z)-2-butenedioate [I; $R^1=R^2=R^3=R^4=H$, $n=7$]

8-[(4-Hydroxyphenyl)amino]octanenitrile was prepared in 80% yield from 33.2 g [0.11 mol] of 4-[(7-bromoheptyl)amino]phenol and 26.5 g (0.52 mol) of sodium cyanide by the first procedure of Example 2, part d, except that DMSO was used in place of DMF as the solvent.

A solution of 21.4 g (0.09 mol) of the free base in 175 mL of acetone was treated with 14.3 g (0.12 mol) of maleic acid in 100 mL of acetone to yield 28.9 g of 8-[(4-hydroxyphenyl)amino]octanenitrile (Z)-2-butenedioate, mp 122°–123° C.

EXAMPLE 5

(a) 8-Bromo-N-(4-hydroxyphenyl)octanamide [IV; $R^1=R^2=R^3=H$, $X=Br$, $n=8$]

was prepared in 91% yield from 27.5 g (0.25 mol) of p-aminophenol and 28.8 g (0.12 mol) of 8-bromooctanoyl chloride according to the procedure of Example 1, part a. In a manner analogous to that of Example 4, part a, 8-bromooctanoyl chloride was prepared from 8-bromooctanoic acid and thionyl chloride, but was used without distillation. The 8-bromo-N-(4-hydroxypheny)octanamide was crystallized from ethanol-water, mp 110°–112° C.

(b) 4-[(8-Bromooctyl)amino]phenol [V; $R^1=R^2=R^3=H$, $X=Br$, $n=8$]

was prepared from 33.9 g (0.11 mol) of 8-bromo-N-(4-hydroxyphenyl)octanamide according to the procedure of Example 1, part b. The crude residue after triturating in ether was evaporated on a rotary evaporator to yield 37.7 g of an oil which was taken to the next step without purification.

(c) 9-[(4-Hydroxyphenyl)amino]nonanenitrile (Z)-2-butenedioate [I; $R^1=R^2=R^3=R^4=H$, $n=8$]

9-[(4-Hydroxyphenyl)amino]nonanenitrile was prepared in 73% yield from 37.5 g (0.11 mol) of 4-[(8-bromooctyl)amino]phenol and 27 g (0.55 mol) of sodium cyanide according to the procedure of Example 4, part c, except that the crude free base was precipitated from ethyl acetate solution with hexane.

A solution of 19.8 g (0.08 mol) of the free base in 120 mL of acetone was treated with a solution of 11.1 g (0.1 mol) of maleic acid in 80 mL of acetone and the solution was diluted with ether. The resulting precipitate was recrystallized from 200 mL of acetonitrile to yield 30.5 g (76%) of 9-[(4-hydroxyphenyl)amino]nonanenitrile (Z)-2-butenedioate, mp 106.5°–107.5° C.

EXAMPLE 6

(a)

6-Bromo-N-(4-hydroxyphenyl)-N-methylhexanamide [IV; $R^1$=$R^2$=H, $R^3$=CH$_3$, X=Br, n=6]

A solution of 100 g (0.29 mol) of 4-methylaminophenol sulfate in 300 mL of water was treated with 750 mL of saturated sodium bicarbonate and the mixture extracted twice with ethyl acetate. The ethyl acetate extracts were combined, washed once with saturated sodium chloride solution, dried over magnesium sulfate and stripped to yield 69 g of the free base of 4-methylaminophenol.

A solution of 69 g (0.56 mol) of 4-methylaminophenol and 73.9 g (0.61 mol) of N,N-dimethylaniline in about 1.5 L of acetone was stirred mechanically under nitrogen in a 3 L flask. A solution of 119.6 g (0.56 mol) of 6-bromohexanoyl chloride in 100 mL of acetone was added as rapidly as the exotherm would allow at about 40° C. The reaction was refluxed for 2 hours on a steam bath, allowed to cool and poured into a solution of about 560 mL of 2N HCl in 2 L of ice. The aqueous solution was extracted twice with ethyl acetate and the ethyl acetate extracts were combined and dried over magnesium sulfate. The ethyl acetate solution was stripped to dryness under high vacuum to yield 143.4 g (85%) of greenish-white, low melting, solid 6-bromo-N-(4-hydroxyphenyl)-N-methylhexanamide.

(b) 4-[(6-Bromohexyl)methylamino]phenol [V; $R^1$=$R^2$=H, $R^3$=CH$_3$, X=Br, n=6]

was prepared from 143.4 g (0.48 mol) of 6-bromo-N-(4-hydroxyphenyl)-N-methylhexanamide according to the procedure of Example 1, part b. The impure product weighing 194 g was used without purification in the following reaction.

(c) 7-[(4-Hydroxyphenyl)methylamino]heptanenitrile [I; $R^1$=$R^2$=$R^4$=H, $R^3$=CH$_3$, n=6]

was prepared from 90 g of impure 4-[(6-bromohexyl)methylamino]phenol according to the first procedure of Example 2, part d. The product, which did not crystallize, was purified by column chromatography on Florisil® brand of magnesia-silica adsorbent using ethyl acetate-hexane in a step gradient from 0% ethyl acetate to 30% ethyl acetate. The fractions containing material which showed a single spot on silica gel thin layer chromatography ($R_f$=0.2 in ethyl acetate-hexane 40:60) were combined and stripped to yield 13.7 g of 7-[(4-hydroxyphenyl)methylamino]heptanenitrile as a low melting solid, mp 42°–44.5° C.

(d)

7-[[4-(Acetyloxy)phenyl]methylamino]heptanenitrile [I; $R^1$=$R^2$=H, $R^3$=CH$_3$, $R^4$=CH$_3$CO, n=6].

A solution of 4 g (0.017 mol) of 7-[(4-hydroxyphenyl)methylamino]heptanenitrile and 2.1 g (0.026 mol) anhydrous sodium acetate in 14 mL (0.17 mol) of acetic anhydride was stirred under nitrogen at room temperature. After 1½ hours 15 mL of ethyl acetate was added followed by 49 mL of absolute ethanol. The reaction was stirred 18 hours at room temperature, cooled, and 61 mL of water was added followed by about 11 g of solid potassium bicarbonate. The layers were separated and the aqueous layer was extracted twice with ethyl acetate. The ethyl acetate extracts were combined, washed three times with saturated sodium bicarbonate solution, two times with saturated sodium chloride solution, and dried over magnesium sulfate. The solution was concentrated in vacuo to 3.4 gm of amber oil which was distilled at 170°–172°/0.08 mm in a Kugelrohr to yield 2.7 g (59%) of 7-[[4-(acetyloxy)phenyl]methylamino]heptanenitrile.

EXAMPLE 7

(a) 6-Bromo-N-(4hydroxy-2-methylphenyl)hexanamide [IV; $R^1$=$R^3$=H, $R^2$=CH$_3$, X=Br, n=6]

was prepared from 48.5 g (0.23 mol) of 6-bromohexanoyl chloride and 60.5 g (0.48 mol) of 4-amino-m-cresol according to the procedure of Example 4, part a. The product was crystallized once from ethanol-water, once from acetone-hexane, and finally from ethanol-water again to yield 51.7 g (76%) of product, mp 94°–99° C., containing a small amount of 4-amino-m-cresol.

(b) 4-[(6-Bromohexyl)amino]-3-methylphenol [V; $R^1$=$R^3$=H, $R^2$=CH$_3$, X=Br, n=6]

was prepared in 88% yield from 45.5 g (0.15 mol) of 6-bromo-N-(4-hydroxy-2-methylphenyl)hexanamide according to the procedure of Example 3, part b. The product was crystallized from acetonitrile-ether, mp 142°–144° C.

(c)

7-[(4-Hydroxy-2-methylphenyl)amino]heptanenitrile monohydrochloride [I; $R^1$=$R^3$=$R^4$=H, $R^2$=CH$_3$, n=6]

was prepared in 89% yield from 46 g (0.14 mol) of 4-[(6-bromohexyl)amino]-3-methylphenol and 36.7 g (0.71 mol) of sodium cyanide by the procedure of Example 3, part c. The monohydrochloride was recrystallized from acetonitrile-ether, mp 148°–149° C.

EXAMPLE 8

(a)

6-Bromo-N-(4-hydroxy-3-methylphenyl)hexanamide [IV; $R^1$=$R^3$=H, $R^2$=CH$_3$, X=Br, n=6]

A solution of 25 g (0.20 mol) of 4-amino-2-methylphenol in about 450 mL of acetone was stirred at room temperature and 20.6 g (0.09 mol) of 6-bromohexanoyl chloride was dripped in over 20 minutes. The reaction was stirred at room temperature for 3 hours then ice-cooled and filtered. The filtrate was stripped in vacuo to a residual oil which was triturated once in 225 mL of 1N HCl and then several times in cold water. The resulting gum was dissolved in absolute ethanol and 28 g of product (95%) were crystallized out by the addition of water, mp 111°–112° C. The product, which contained a small amount of 4-amino-2-methylphenol, was used as is in the following reaction.

(b) 4-[(6-Bromohexyl)amino]-2-methylphenol [V; $R^1$=$R^3$=H, $R^2$=CH$_3$, X=Br, n=6]

was prepared in 94% yield from 28 g (0.09 mol) of 6-bromo-N-(4-hydroxy-3-methylphenyl)hexanamide according to the procedure of Example 3, part b. The product was crystallized from acetonitrile-ether, mp 144°–146° C.

(c)
7-[(4-Hydroxy-3-methylphenyl)amino]heptanenitrile monohydrochloride [I; $R^1=R^3=R^4=H$, $R^2=CH_3$, n=6]

was prepared in 65% yield from 28.3 g (0.09 mol) of 4-[(6-bromohexyl)amino]-2-methylphenol and 22.6 g (0.44 mol) of sodium cyanide by the procedure of Example 3, part c. The hydrochloride was crystallized from acetonitrile-ether and then recrystallized from absolute ethanol-ether, mp 181°–182° C.

EXAMPLE 9

(a) 6-Bromo-N-(3,5-dichloro-4-hydroxyphenyl)hexanamide [IV; $R^1=R^2=Cl$, $R^3=H$, X=Br, n=6]

was prepared in 89% yield from 24.4 g (0.14 mol) of 4-amino-2,6-dichlorophenol, 18.1 g (0.15 mol) of N,N-dimethylaniline and 28.8 g (0.14 mol) of 6-bromohexanoyl chloride according to the procedure of Example 6, part a, except that the reaction was cooled on ice during the addition and was stirred at room temperature rather than refluxed. The product was crystallized from ethanol-water, mp 113°–114° C.

(b) 4-[(6-Bromohexyl)amino]-2,6-dichlorophenol [V; $R^1=R^2=Cl$, $R^3=H$, X=Br, n=6]

was prepared in 82% yield from 42.5 g (0.12 mol) of 6-bromo-N-(3,5-dichloro-4-hydroxyphenyl)hexanamide according to the procedure of Example 1, part b. The solid, which was obtained after the evaporation of methanol, ethanolic HCl, and methyl borate, was triturated two times in acetonitrile to yield 37.1 g of product, mp 182°–183° C.

(c) 7-[(3,5-Dichloro-4-hydroxyphenyl)amino]heptanenitrile monohydrochloride [I; $R^1=R^2=Cl$, $R^3=R^4=H$, n=6]

A mixture of 23.8 g (0.49 mol) of sodium cyanide in 70 mL of DMSO under nitrogen was heated in an oil bath at 78°–85° C. and a solution of 36.6 g (0.10 mol) of 4-[(6-bromohexyl)amino]-2,6-dichlorophenol in 120 mL of DMSO was dripped in over 1¼ hours. The mixture was heated at 70° C. for another ½ hour, cooled to 50° C., diluted with 200 mL of ethyl acetate, and then cooled to room temperature. The mixture was filtered and the precipitate washed with 500 mL of ethyl acetate. The filtrate and washes were combined and shaken with 400 mL of water. The aqueous phase was extracted three times with fresh ethyl acetate, and the ethyl acetate extracts were combined and washed twice with saturated sodium chloride solution, dried over magnesium sulfate, and evaporated to give 37.8 g of an oil. The oil was dissolved in 50 mL of ethanol, acidified with ethereal HCl, and the resulting precipitate filtered and washed with ether-ethanol. The precipitate was dissolved in 200 mL of ethanol, warmed, cooled and filtered to remove an insoluble impurity. The filtrate was stripped and the residue crystallized from acetonitrile-ether and then recrystallized from ethanol-ether to yield 12.7 g (39%) of 7-[(3,5-dichloro-4-hydroxyphenyl)amino]heptanenitrile monohydrochloride, mp 187°–189° C.

EXAMPLE 10

(a) Methyl 5-[(6-bromo-1-oxohexyl)amino]-2-hydroxybenzoate [IV; $R^1=R^3=H$, $R^2=COOCH_3$, X=Br, n=6]

was prepared in quantitative yield from 40.0 g (0.24 mol) of methyl-5-aminosalicylate, 32.0 g (0.26 mol) of N,N-dimethylaniline and 46.5 g (0.22 mol) of 6-bromohexanoyl chloride according to the procedure of Example 9, part a. The methyl 5-aminosalicylate was obtained by Fischer esterification of 5-aminosalicylic acid. The product was not recrystallized, but was obtained directly from trituration in 1N HCl, mp 100°–102° C.

(b) 4-[(6-Bromohexyl)amino]-2-(hydroxymethyl)phenol [V; $R^1=R^3=H$, $R^2=CH_2OH$, X=Br, n=6]

was prepared in 98% yield from 34.4 g (0.10 mol) of methyl 5-[(6-bromo-1-oxohexyl)amino]-2-hydroxybenzoate and 620 mL (0.62 mol) of borane-THF complex according to the procedure of Example 3, part b. The product was crystallized from acetonitrile-ether, mp 132°–134° C.

(c) 7-[[4-Hydroxy-3-(hydroxymethyl)phenyl]amino]heptanenitrile monohydrochloride [I; $R^1=R^3=R^4=H$, $R^2=CH_2OH$, n=6]

was prepared in 41% yield from 33 g (0.10 mol) of 4-[(6-bromohexyl)amino]-2-(hydroxymethyl)phenol and 25.1 g (0.49 mol) of sodium cyanide by the procedure of Example 3, part c. The hydrochloride salt was obtained from acetonitrile-ethanolic HCl solution by precipitation with ether and was recrystallized from absolute ethanol-acetone-ether, mp 134°–136° C.

EXAMPLE 11

(a) 6-Bromo-N-(2-fluoro-4-hydroxyphenyl)hexanamide [IV; $R^1=R^3=H$, $R^2=F$, X=Br, n=6].

To a solution of 50 g (0.45 mol) of 3-fluorophenol in 55 mL of acetic acid stirred mechanically at 0° C. was added a solution of 45.5 ml (0.75 mol) of concentrated HNO₃ in 125 ml of acetic acid over the course of ½ hour. The reaction was stirred at 0° for ¾ hour, diluted with 950 ml of water, stirred, and extracted three times with ether. The combined ether layers were washed twice with saturated sodium chloride solution then five times with saturated sodium bicarbonate solution then dried over magnesium sulfate. The ether solution was stripped to about 400 mL and poured with mechanical stirring into 800 mL of 2M sodium carbonate. The sodium salt of the product initially precipitated as an oil and then crystallized. It was cooled, stirred, filtered off and washed with a little ethyl acetate and then hexane. The sodium salt was dissolved in water, cooled and acidified with 6N HCl. The mixture was extracted three times with ether and the combined ether layers were washed twice with saturated sodium chloride solution and dried over magnesium sulfate. The solvent was stripped in vacuo, and 14.1 g (20%) of 3-fluoro-4-nitrophenol were crystallized from acetonitrile, m.p. 90°–93° C. The mother liquors contained a substantial quantity of 3-fluoro-6-nitrophenol.

The 14 g (0.09 mol) of 3-fluoro-4-nitrophenol from above was combined with 55 mL (0.66 mol) of concentrated HCl, 55 mL of H₂O, and 0.5 mL of octanol and stirred mechanically. To this mixture was added 33 g (0.28 mol) of mossy tin and the mixture was heated on a steam bath to initiate the reaction. After the reaction had subsided (8–10 minutes), 92 mL of concentrated HCl in 160 mL of water was added. The reaction was stirred on the steam bath for ½ hour and filtered hot. The filtrate was cooled and made basic with solid sodium bicarbonate. The resulting salts were filtered off and washed with ethyl acetate. The filtrate was extracted three times with ethyl acetate; all of the ethyl acetate extracts were combined, washed twice with saturated sodium chloride solution, and dried over magnesium sulfate. The solvent was stripped in vacuo and the resulting residue dissolved and stripped twice with toluene then ethanol then acetonitrile. The solid residue was triturated in hexane, filtered and washed to yield 10.9 g (96%) of 4-amino-3-fluorophenol, mp 138°–140° C.

The 10.9 g (0.09 mol) of 4-amino-3-fluorophenol from above was reacted with 8.96 g (0.04 mol) of 6-bromohexanoyl chloride according to the procedure of Example 3, part a. 6-Bromo-N-(2-fluoro-4-hydroxyphenyl) hexanamide was obtained in 98% yield after crystallization from acetonitrile, mp 66°–69° C.

(b) 4-[(6-Bromohexyl)amino]-3-fluorophenol [V; $R^1=R^3=H$, $R^2=F$, $X=Br$, $n=6$]

was prepared in essentially quantitative yield from 12.2 g (0.04 mol) 6-bromo-N-(2-fluoro-4-hydroxy-phenyl) hexanamide according to the procedure of Example 3, part b. The product was crystallized from 50 mL of acetonitrile by careful addition of ether, mp 103°–106° C.

(c) 7-[(2-Fluoro-4-hydroxyphenyl)amino]heptanenitrile monohydrochloride [I; $R^1=R^3=R^4=H$, $R^2=F$, $n=6$]

was prepared in 81% yield from 13 g (0.04 mol) 4-[(6-bromohexyl)amino]-3-fluorophenol and 10.2 g (0.20 mol) of sodium cyanide according to the procedure of Example 3, part c. The monohydrochloride was crystallized from acetonitrile ether, m.p. 123°–125° C.

EXAMPLE 12

11-[(4-Hydroxyphenyl)amino]undecanenitrile [I; $R^1=R^2=R^3=R^4=H$, $n=10$].

By a process substantially similar to that of Example 5 it is contemplated that 11-[(4-hydroxyphenyl)amino]undecanenitrile may be prepared from 4-aminophenol and 10-bromodecanoic acid.

EXAMPLE 13

13-[(4-Hydroxy-3-methoxyphenyl)amino]tridecanenitrile [I; $R^1=OCH_3$, $R^2=R^3=R^4=H$, $n=12$].

By a process substantially similar to that of Example 5, it is contemplated that 13-[(4-hydroxy-3-methoxyphenyl)amino]tridecanenitrile may be prepared from 4-amino-2-methoxyphenol and 12-bromododecanoic acid. 4-Amino-2-methoxyphenol is synthesized by the method of Heidelberger and Jacobs *J. Am. Chem. Soc.* 41, 1450 (1919).

EXAMPLE 14

7-[[4-[(1-Oxobutyl)oxy]phenyl]methylamino]heptanenitrile [I; $R^1=R^2=H$, $R^3=CH_3$m $R^4=CH_3CH_2CH_2CO$, $n=6$].

By a process substantially similar to that of Example 6, part d, it is contemplated that 7-[[4-[(1-oxobutyl)oxy]phenyl]methylamino]heptanenitrile may be prepared from 7-[(4-hydroxyphenyl)methylamino]heptanenitrile, butyric anhydride, and sodium butyrate.

EXAMPLE 15

7-[(2-Bromo-4-hydroxyphenyl)amino]heptanenitrile [I; $R^1=Br$, $R^2=R^3=R^4=H$, $n=6$].

By a process substantially similar to that of Example 11, it is contemplated that 7-[(2-bromo-4-hydroxyphenyl)amino]heptanenitrile may be prepared from 3-bromophenyl and 6-bromohexanoyl chloride.

EXAMPLE 16

7-[(4-Hydroxyphenyl) (1-methylethyl)amino]heptanenitrile [I; $R^1=R^2=R^4=H$, $R^3=CH(CH_3)_2$, $n=6$].

By a process substantially similar to that of Example 6, parts a-c, it is contemplated that 7-[(4-hydroxyphenyl)(1-methylethyl)amino]heptanenitrile may be prepared from 4-(isopropylamino)phenol and 6-bromohexanoyl chloride. 4-(Isopropylamino)phenol is available by reductive alkylation of 4-aminophenol with acetone in sodium acetate-acetic acid buffered ethanol using sodium borohydride at 0° C.

EXAMPLE 17

7-[[4-(Acetyloxy)phenyl]amino]heptanenitrile [I; $R^1=R^2=R^3=H$, $R^4=CH_3CO$, $n=6$].

It is contemplated that 7-[(4-hydroxyphenyl)amino]heptanenitrile of Example 2, part d may be converted to 7-[[4-(acetyloxy)phenyl]amino]heptanenitrile by reaction with di-t-butyl dicarbonate according to the method of Wuensch [*Hoppe-Seyler Z. Physiol. Chem.* 357, 1651 (1976)] followed by acetylation by a process substantially similar to that of Example 6, part d, and finally cleavage of the t-Boc group using 3N HCl in ethyl acetate.

EXAMPLE 18

7-[[2-Hydroxy-4-(1-methylethyl)phenyl]amino]heptanenitrile [I; $R^1=CH(CH_3)_2$, $R^2=R^3=R^4=H$, $n=6$]

By a process substantially similar to that of Example 11, it is contemplated that 7-[[2-hydroxy-4-(1-methylethyl)phenyl]amino]heptanenitrile may be prepared from 3-isopropylphenol and 6-bromohexanoyl chloride.

EXAMPLE 19

11-[[4-Hydroxy-2-(methylthio)phenyl]amino]undecanenitrile [I; $R^1=SCH_3$, $R^2=R^3=R^4=H$, $n=11$]

By a process substantially similar to that of Example 5, it is contemplated that 11-[[4-hydroxy-2-(methylthio)phenyl]amino]undecanenitrile may be prepared from 4-amino-3-(methylthio)phenol and 11-bromoundecanoic acid. 4-amino-3-(methylthio)phenol is synthesized by the method of Focella et al. *Can. J. Chem.* 50, 2025 (1972).

The compounds of formula I have been found to inhibit lipoxygenase activity in biological systems, thus indicating their usefulness as anti-asthmatic agents.

Slow reacting substance of anaphylaxis (SRS-A) is a descriptive term for a family of lipoxygenase metabolic products of arachidonic acid designated as the leukotrienes. These substances are potent contractile agents of vascular and pulmonary smooth muscle. The relationship of SRS-A to asthma was first characterized by Brockelhurst [*Rev. in Adv. Drug Res.* 19, 109 (1970)]

who identified the material as being present subsequent to specific antigen challenge of living tissue obtained from asthmatic patients. Herxheimer and Stressmann [*J. Physiol.* 165, 78P (1953)] first demonstrated that aerosolized guinea pig SRS-A induced bronchospasm in man. This observation has been more recently confirmed using purified leukotrienes.

Recent studies have indicated that lipoxygenase inhibiting compounds may have therapeutic potential in treating disease states other than asthma, e.g. bronchitis, acute inflammation, arthritis, psoriasis, cardiovascular insufficiency and myocardial infarct.

The primary screening test used is a determination of the inhibition of lipoxygenase and cyclooxygenase derived from rat basophilic leukemia (RBL-1) cells. The test was carried out according to the following procedure:

Single cell suspensions of RBL-1 cells are homogenized to obtain the microsomal fraction containing lipoxygenase and cyclooxygenase. Test compounds are added to the enzyme-containing homogenate for a 5 min. preincubation period at 37° C. prior to the addition of $^{14}C$-arachidonic acid substrate. Following incubation at 37° C. for 15 min., the reaction is stopped by the addition of 2M formic acid and the enzyme-substrate products are extracted into chloroform. An aliquot of the extract is evaporated to dryness, reconstituted in ether to 1/10 original volume, spotted on thin layer chromatography plates and chromatographed. The peak areas of radioactivity representing the products are located by scanning the plates. The quantity of products formed is estimated by measuring the height of the radioactivity peaks observed on the chromatographic scans. Alternatively, the areas of radioactivity are scraped from the plate and the $^{14}C$ quantitated by scintillation counting. The percent inhibition in the formation of the cyclooxygenase product prostaglandin $D_2$, designated as $C_1$, and lipoxygenase products 5,12-di-HETE and 5-HETE, designated $L_1$ and $L_2$ respectively, are shown. Compounds with >50% inhibition of $L_1$ and $L_2$ at a screening concentration of 1 $\mu M$ are considered active.

The activity in vivo was measured by the effect on the SRS-A component of immunologically induced bronchoconstriction in guinea pigs. The test was carried out according to the following procedure:

Outbred female guinea pigs were sensitized to egg albumin by a 1 mL ip injection of a 1 mg/mL egg albumin alum suspension. Twelve to sixteen days after immunization, the animals were used for the test. They were anesthetized with urethane (1.5 gm/kg ip) and surgically prepared with a jugular vein canula connected to a three-way stopcock for administration of drugs and antigen challenge. The trachea was cannulated and the animal artificially respired. The intratracheal pressure was continuously recorded and expressed in mm Hg. Naproxen sodium (10 mg/kg) and pyrilamine maleate (0.3 mg/kg) in phosphate buffered saline, pH 7.2, were administered intravenously in a single solution seven minutes prior to antigen challenge. Propranolol (0.1 mg/kg) was also given iv three minutes prior to challenge with egg albumin (300 $\mu g$/kg iv). The animals were dosed orally with compounds in water or in a vehicle of 3% corn starch, 5% polyethylene glycol 400, and 0.34% Tween 8 TM in water at one or four hours before challenge. Results were recorded as the maximum increase in intratracheal pressure following antigen challenge. Activity of the compounds was measured as percent inhibition of the mean peak intratracheal pressure in the group of dosed animals in comparison to the mean peak intratracheal pressure in the group of vehicle treated animals. The results are expressed in terms of % inhibition.

The following table summarizes the results obtained from the testing of specific compounds of the invention.

| Example No. | % Inhibition in vitro at 1 $\mu M$ | | | % Inhibition in vivo at 100 mg/kg p.o. | |
|---|---|---|---|---|---|
| | $C_1$ | $L_1$ | $L_2$ | at 1 hour | at 4 hours |
| 1c | 0 | 100 | 100 | | |
| 2d | 42 | 92 | 98 | 66 | 61 |
| 3c | 0 | 100 | 100[a] | 4 | 11 |
| 4c | 0 | 100 | 100 | 17 | 76 |
| 5c | 0 | 82 | 95[a] | 0 | 25 |
| 6c | 28 | 100 | 100 | 6 | |
| 6d | 14 | 91 | 85[a] | | |
| 7c | 0 | 79 | 65[a] | 66[b] | 86[b] |
| 8c | 13 | 100 | 100 | | |
| 9c | 9 | 89 | 95[a] | | |
| 10c | 10 | 100 | 100 | | |
| 11c | 22 | 86 | 93[a] | 7 | 30 |

[a]The in vitro inhibitions given are at 0.1 $\mu M$.
[b]The inhibition in vivo is at a dose of 300 mg/kg p.o.

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

For the treatment of asthma the compounds of the invention may also be administered by inhalation. For such use suitable compositions may comprise a suspension or solution of the active ingredient, preferably in the form of a salt, such as the hydrochloride salt, in water, for administration by means of a conventional nebulizer. Alternatively, the compositions may comprise a suspension or solution of the active ingredient in a conventional liquified propellant such as dichloro difluoromethane or dichlorotetrafluoroethane to be administered from a pressurized container fitted with an aerosol valve suitable for release of the pressurized composition. Preferably the aerosol valve is a metered valve, that is, one which on activation releases a predetermined effective dose of the aerosol composition. When the medicament is not soluble in the propellant it may be necessary to add a cosolvent such as ethanol, dipropylene glycol, isopropyl myristate, or surface active agent to the composition in order to suspend the medicament in the propellant medium, and such surface active agents may be any of those commonly used for this purpose such as lecithin. The compounds of the invention may also be administered in the form of powders by means of a suitable insufflator device, and in this case the fine particle size powders of the active ingredient may be mixed with a diluent material such as lactose.

The percentage of active component in the composition and method for treating or preventing asthma can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus only be determined by the clinician considering all criteria and utilizing his best judgement on the patient's behalf.

We claim:

1. A compound of the formula

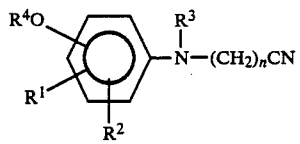

or acid-addition salt thereof wherein: $R^1$ and $R^2$ may be the same or different and are chosen from the group consisting of hydrogen, lower-alkyl, lower-alkoxy, lower-alkylthio, hydroxy lower-alkyl, and halo; $R^3$ is hydrogen or lower-alkyl; $R^4O$ is 2- or 4-hydroxy or 2- or 4-lower-acyloxy; and n is an integer from four to twelve.

2. A compound according to claim 1 wherein n is four to five.

3. A compound according to claim 1 wherein n is an integer from nine to twelve.

4. A compound according to claim 1 wherein n is an integer from six to eight.

5. A compound according to claim 4 wherein $R^1$ and $R^2$ may be the same or different and are chosen from the group consisting of hydrogen, methyl, chlorine, fluorine and hydroxymethyl.

6. A compound according to claim 5 wherein $R^3$ is hydrogen or methyl.

7. A compound according to claim 6 wherein $R^4$ is acetyl.

8. A compound according to claim 6 wherein $R^4$ is hydrogen.

9. 5-[(4-Hydroxyphenyl)amino]pentanenitrile or acid-addition salt thereof according to claim 2.

10. 7-[(4-Hydroxyphenyl)amino]heptanenitrile or acid-addition salt thereof according to claim 8.

11. 7-[(2-Hydroxyphenyl)amino]heptanenitrile or acid-addition salt thereof according to claim 8.

12. 8-[(4-Hydroxyphenyl)amino]octanenitrile or acid-addition salt thereof according to claim 8.

13. 9-[(4-Hydroxyphenyl)amino]nonanenitrile or acid-addition salt thereof according to claim 8.

14. 7-[(4-Hydroxyphenyl)methylamino]heptanenitrile or acid-addition salt thereof according to claim 8.

15. 7-[[4-(Acetyloxy)phenyl]methylamino]heptanenitrile or acid-addition salt thereof according to claim 7.

16. 7-[(4-Hydroxy-2-methylphenyl)amino]heptanenitrile or acid-addition salt thereof according to claim 8.

17. 7-[(4-Hydroxy-3-methylphenyl)amino]heptanenitrile or acid-addition salt thereof according to claim 8.

18. 7-[(3,5-Dichloro-4-hydroxyphenyl)amino]heptanenitrile or acid-addition salt thereof according to claim 8.

19. 7-[[4-Hydroxy-3-(hydroxymethyl)phenyl]amino]heptanenitrile or acid-addition salt thereof according to claim 8.

20. 7-[(2-Fluoro-4-hydroxyphenyl)amino]heptanenitrile or acid-addition salt thereof according to claim 8.

21. A composition for inhibiting lipoxygenase activity which comprises a compound according to claim 1 together with one or more pharmaceutically acceptable excipients or diluents.

22. A composition for inhibiting lipoxygenase activity which comprises a compound according to claim 6 together with one or more pharmaceutically acceptable excipients or diluents.

23. A composition for inhibiting lipoxygenase activity which comprises 7-[(4-hydroxyphenyl)amino]heptanenitrile according to claim 10 together with one or more pharmaceutically acceptable excipients or diluents.

24. An antiasthmatic composition which comprises a compound according to claim 1 together with one or more pharmaceutically acceptable excipients or diluents.

25. An antiasthmatic composition which comprises a compound according to claim 6 together with one or more pharmaceutically acceptable excipients or diluents.

26. An antiasthmatic composition which comprises 7-[(4-hydroxyphenyl)amino]heptanenitrile according to claim 10 together with one or more pharmaceutically acceptable excipients or diluents.

27. A method for inhibiting lipoxygenase activity in a mammal which comprises administering to said mammal a pharmacologically effective amount of a composition according to claim 21.

28. A method for inhibiting lipoxygenase activity in a mammel which comprises administering to said mammal a pharmacologically effective amount of a composition according to claim 22.

29. A method for inhibiting lipoxygenase activity in a mammal which comprises administering to said mammal a pharmacologically effective amount of a composition according to claim 23.

30. A method of treating or preventing asthma in a mammal which comprises administering to said mammal an antiasthmatically effective amount of a composition according to claim 24.

31. A method of treating or preventing asthma in a mammal which comprises administering to said mammal an antiasthmatically effective amount of a composition according to claim 25.

32. A method of treating or preventing asthma in a mammal which comprises administering to said mammal an antiasthmatically effective amount of a composition according to claim 26.

* * * * *